Figure 1:
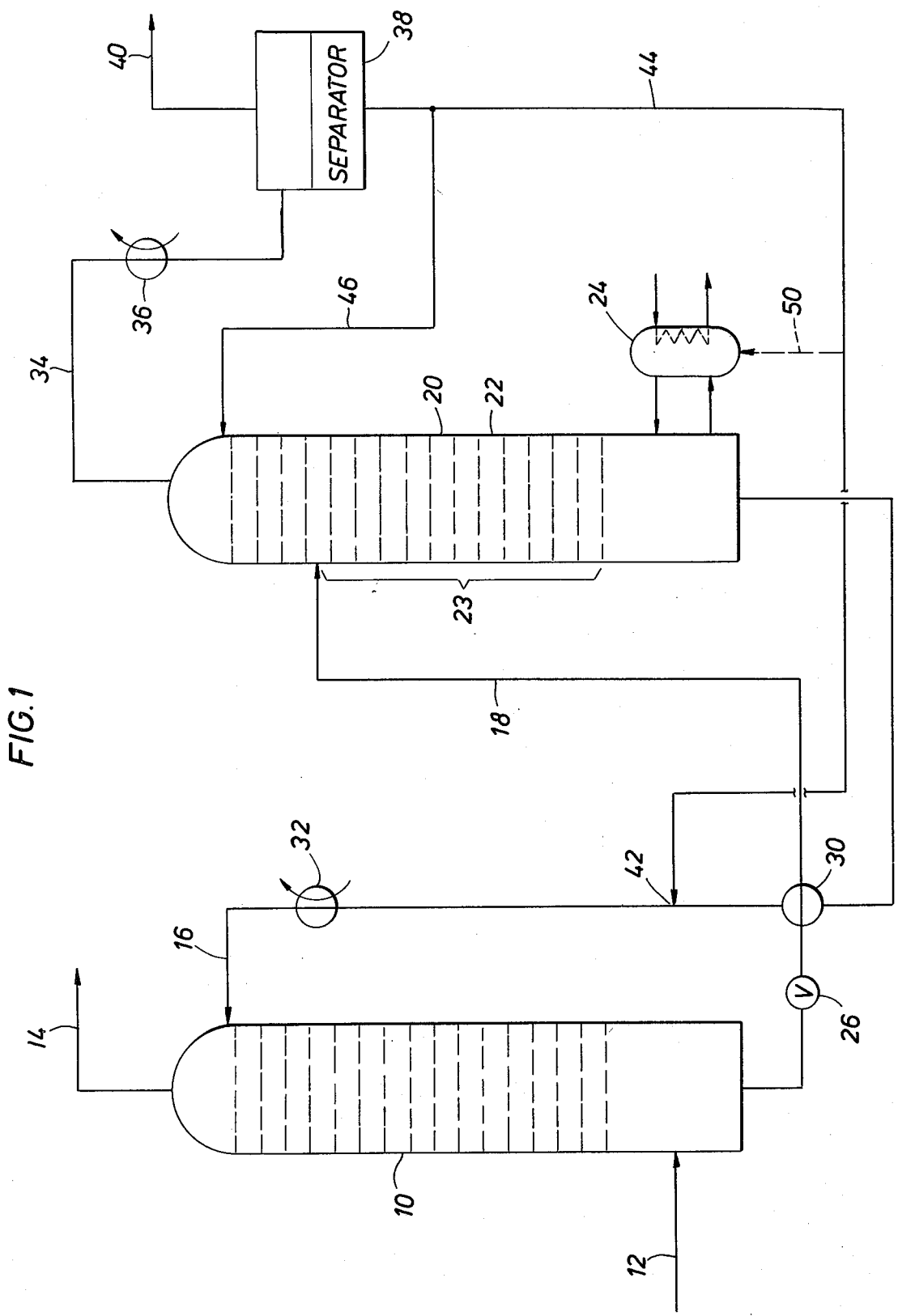

United States Patent [19]

van de Kraats et al.

[11] 4,452,763

[45] Jun. 5, 1984

[54] PROCESS FOR REGENERATION OF SOLVENTS IN HYDROGEN SULFIDE REMOVAL FROM GASES

[76] Inventors: Eduard J. van de Kraats; Richard C. Darton, both of 3, Badhuisweg, Amsterdam, Netherlands

[21] Appl. No.: 341,717

[22] Filed: Jan. 22, 1982

Related U.S. Application Data

[63] Continuation of Ser. No. 108,090, Dec. 28, 1979, abandoned.

[30] Foreign Application Priority Data

Dec. 28, 1978 [GB] United Kingdom ............... 50121/78

[51] Int. Cl.³ ............................................ B01D 53/34
[52] U.S. Cl. .................................... 423/228; 423/220; 423/229; 423/243; 55/73
[58] Field of Search ............... 423/220, 223, 226, 228, 423/233, 232, 229, 243; 55/68, 73

[56] References Cited

U.S. PATENT DOCUMENTS

| | | | |
|---|---|---|---|
| 2,157,879 | 5/1939 | Zublin | 423/229 X |
| 2,466,183 | 4/1949 | Reed | 423/229 |
| 2,487,576 | 11/1949 | Meyers | 423/228 |
| 2,863,527 | 12/1958 | Herbert et al. | 55/73 |
| 2,886,405 | 5/1959 | Benson et al. | 423/223 |
| 3,101,996 | 8/1963 | Bresler et al. | 423/229 |
| 3,266,886 | 8/1966 | Bally et al. | 423/229 |
| 3,288,557 | 11/1966 | Bresler | 423/229 |
| 3,347,621 | 10/1967 | Papadopoulos et al. | 423/226 |
| 3,851,041 | 11/1974 | Eickmeyer | 423/228 X |
| 4,085,192 | 4/1978 | Van Scoy | 423/226 |
| 4,160,810 | 7/1979 | Benson et al. | 423/228 |

FOREIGN PATENT DOCUMENTS

| | | | |
|---|---|---|---|
| 1273115 | 7/1968 | Fed. Rep. of Germany | 423/229 |
| 2531898 | 1/1977 | Fed. Rep. of Germany | 423/242 |

*Primary Examiner*—Earl C. Thomas

[57] ABSTRACT

Process for regeneration of a solvent for preferentially absorbing acid gases. The solvent, which comprises between 5 and 55 percent by weight water, is steam stripped in a regenerator, and vapor leaving the regenerator with the acid gases is condensed. The resulting condensate is returned to the solvent downstream of the regeneration zone. The condensate may be partially or wholly recirculated to the upper part of the regenerator provided that the majority of it is withdrawn above the regeneration zone. Some of the condensate may be added back to the solvent at the bottom of the regenerator or in a reboiler associated with the regenerator.

4 Claims, 2 Drawing Figures

PROCESS FOR REGENERATION OF SOLVENTS IN HYDROGEN SULFIDE REMOVAL FROM GASES

This is a continuation of application Ser. No. 108,090, filed Dec. 28, 1979, and now abandoned.

BACKGROUND OF THE INVENTION

The invention relates to treatment of fluids to remove acid gases, in which the fluid is contacted with a solvent which preferentially absorbs the acid gases. More particularly, the invention is concerned with the regeneration of a solvent of the type specified for reuse.

The term "absorbing solvent", as used herein, shall mean either an aqueous solution of a chemical solvent or solution comprising a combined chemical solvent and physical solvent with some water, which solutions are capable of absorbing acid gases. The chemical solvent part comprises one or more basic amines and may comprise a primary, secondary and/or tertiary amine. Alkanolamines are suitable, especially those having 1 to 4 and preferably 2 to 3 carbon atoms per alkanol radical, while dialkanolamines are particularly advantageous. Typical examples are monoethanolamine, diethanolamine, diisopropanolamine, diethylethanolamine, methyldiethanolamine and mixtures thereof. Other amines which can be used are alkylamines, phenyl alkylamines, alkoxyalkyl and alkoxyaryl amines. Typical of these are methylethyl amine, phenyl ethylamine, and methoxy diethyldiamine. Aliphatic amines having between 2 and 8 amine groups may also be used. Examples of such amines are triethylenetetramine, tetraethylenepentamine, and derivatives thereof.

The physical solvent part comprises at least one component selected from cyclotetramethylene sulphones, aliphatic acid amides, perhalo alkanes, N-alkylated pyrrolidones or N-alkylated piperidones or their derivatives.

The derivatives from the basic sulphone are cyclotetramethylene sulphone or thiophene tetrahydro-1,1-dioxide, which is also known as sulfolane, and should have not more than four, more preferably not more than two alkyl substituents in the tetramethylene sulphone ring. Sulfolane is the preferred species of this class of compounds. Suitable amides are the dialkyl-N-substituted aliphatic acid amides, a preferred species being dimethyl formamide. The alkyl groups directly attached to the nitrogen atom should have from 1 to 4 carbon atoms each, while an acid with 1 to 4 carbon atoms per molecule is preferred. Apart from dimethyl formamide, other species in this sub-class include methyl ethyl formamide, diethyl formamide, propyl methyl formamide, dibutyl formamide, dimethyl acetamide, methyl ethyl acetamide, formamide and acetamide. Suitable perhaloalkanes include perfluoro alkanes such as perfluoro ethane and perfluoro butane as well as perchloralkanes such as perchloro propane. Where an N-alkylated pyrrolidone or an N-alkylated piperidone is used, although the alkyl substitutent on the nitrogen atom may be any alkyl group, alkyl groups with 1 to 4 carbon atoms are preferred, and N-methyl pyrrolidone is particularly suitable.

For the purposes of this invention, carbonyl sulphide (COS) will be considered to be an acid gas.

In a typical process for removing acid gases from a fluid, the fluid is contacted with an absorbing solvent which preferentially absorbs the acid gases, the solvent which has thus absorbed acid gases being referred to as "fat solvent". The fat solvent is regenerated by stripping the absorbed acid gases from it using steam. The stripped, or lean solvent is then recirculated for reuse and the released acid gases are removed for further treatment. In such a process, the major part of the operating costs results from the steam consumption required for the regeneration step.

It is an object of the present invention to improve the efficiency of the regeneration of a solvent of the type specified.

SUMMARY OF THE INVENTION

In accordance with the invention, absorbed gases are stripped from the fat solvent in a regenerator by heating it so that at least a part of the water present in the fat solvent boils, and the greater part of the absorbed gases are released from said solvent, producing a lean absorbing solvent. The resulting water vapor and gases are removed from the regenerator, the water vapor leaving the regenerator is condensed, and at least a portion of the resulting condensate is returned to the lean, absorbing solvent after it has left the regeneration zone of the regenerator. As used herein, the term "regeneration zone" is used here to mean that zone in the regenerator in which the solvent is contacted with rising vapor, and excluding any reboiling zone at the bottom of the vessel or exterior to it. The object of the invention is the saving of energy required for regenerating the solvent.

Reducing the water content means that, at the same temperature, the absorbing solvent has a lower total vapor pressure. Because of the lower total pressure the volume of the gas stream is relatively greater for a given mass flow of steam. This will cause the partial pressure of the acid component to be further from its equilibrium value and hence the driving force for mass transfer (stripping) to be greater. However, it will usually not be possible to operate the regenerator at lower pressure since this is determined by downstream units. In this case the pressure may be kept the same, and, providing there are no heat transfer constraints, the temperature may be raised. This again is advantageous for the stripping, since at a higher temperature the acid gas is less soluble.

In addition, the reduced proportion of water in the solvent reduces the strength of the chemical bond between the solvent and the acid gas, which lowers the resistance of the absorbed gases to stripping For the invention to make a significant effect on the energy consumption required for regeneration of an absorbing solvent, the solvent should not contain so much water that its removal from the regeneration zone does not substantially alter the thermodynamic and chemical conditions obtaining there. Some water/steam should, nevertheless, remain in the regenerator as this is necessary for the removal of the $H_2S$ from the regenerator. Furthermore, sufficient water should be present in the solvent that a significant proportion of it can be withdrawn from the regenerator without the temperature at the bottom of the regenerator becoming unstable due to excessively low partial pressure of the remaining water; a remedy for this phenomenon is, however, proposed below.

The absorbing solvent will contain between 5 and 55 percent by weight of water, preferably from 10 to 35 percent by weight of water. The optimum conditions obtain when the absorbing solvent comprises a chemical and a physical part and contains between 15 and 25 %w water. Then up to about two thirds, but more usually between one third and a half, of the water may by-pass the regeneration zone so that the effect of the invention is most marked, and a reduction of stripping steam consumption of some 20% to 25% may be obtainable, though more usually it will be in the order of 15%.

Some of the recondensed water may be recirculated to the upper part of the regenerator as a water wash in order to prevent or at least reduce the loss of the solvent from the regenerator by being carried downstream to the acid gas treatment plant. Alternatively, the condensate may be used to wash the acid gas in a small vessel external to the regenerator.

In a particularly elegant embodiment of the invention, the condensate is partly or wholly returned to the upper part of the regenerator where it is used to wash the rising gas to remove traces of the solvent from it. The condensate is then withdrawn a little lower down the column by suitable means, such as a so-called total draw-off tray. From an energy point of view there is little disadvantage in recirculating the condensate in such a way, but it has the advantage of reducing the loss of solvent from the regenerator.

In order to maintain the water inventory in the absorbing solvent, the condensate is added back to it after, i.e., downstream of, the regeneration zone conveniently after the lean solvent has left the regenerator. Depending upon the temperature of the condensate, it will be added to the lean solution before or after it has been cooled by heat exchange with the fat solvent and/or in a cooler.

In another embodiment, at least a part of the condensate is added back to the absorbent in the reboiler or at the bottom of the regeneration vessel, i.e., after the regeneration zone. This can considerably simplify the control of the operation of the regenerator where the solvent is highly concentrated and little water is present. In this case, the low proportion of water in the solvent can result in a loss of temperature stability because of the excessive influence of the water vapor partial pressure on the total pressure in the regenerator. By adding at least a part of the condensate back into the reboiler, it increases the bulk of the water, thus reducing the concentration of the solvent in the reboiler without affecting the improved thermodynamic conditions in the regeneration zone. The extra heat needed to reheat the increased bulk of water to the regeneration operating temperature is small compared with the benefit obtained.

The invention equally relates to apparatus for carrying out a process in accordance with the invention. Such apparatus comprises an absorber in which solvent is arranged to contact a stream containing acid gas impurities, in order selectively to absorb the acid gas impurities, and a regeneration vessel in which the absorbed acid gases are arranged to be released from the absorbent by stream stripping. The gas outlet of the regenerator is provided with condenser means arranged to condense vapor leaving the regenerator and a liquid line from the condenser means to a place in the solvent circuit downstream of the regeneration zone of the regenerator with respect to the flow of the solvent.

A line may also be provided from the condenser to the upper part of the regenerator, but where a significant proportion of the condensate is intended to be refluxed, the regenerator is provided with means, such as a total draw-off tray, for withdrawing substantially all the condensate above the regeneration zone.

The liquid line from the condenser may rejoin the solvent circuit either in a reboiler associated with the bottom of the regenerator, or in the bottom of the regenerator itself, after the regenerator, or downstream of the regeneration zone of the regenerator, or at one or more of these points, valve means being provided to control the proportion, if any, of the solvent reentering the solvent circuit or the regenerator at a particular point.

Figure 2:
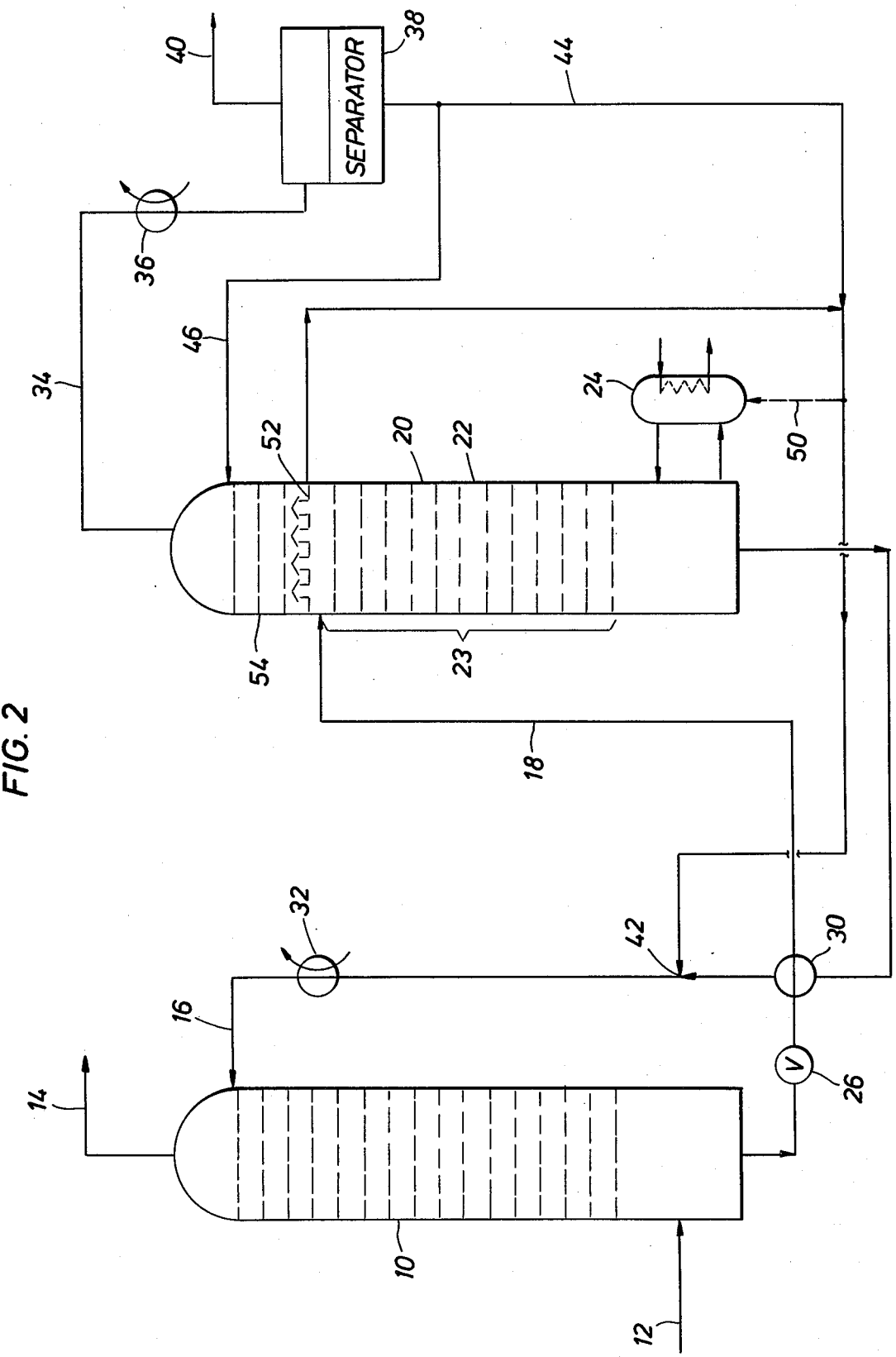

The invention will now be further described by way of example with reference to the accompanying drawings in which FIG. 1 is a schematic block diagram of a typical acid gas absorption plant which has been modified in order to take advantage of the invention, and FIG. 2 shows an alternative embodiment of the invention.

A hydrocarbon feed containing acid gas enters the lower end of an absorption vessel 10 by line 12. As shown, the vessel 10 is provided with a number of contacting trays represented by broken lines.

In the vessel 10 the feed flows upwardly in countercurrent to an absorbing solvent which removes the acid gases from it. The treated feed leaves from the top of the vessel by line 14.

Lean solvent enters the vessel 10 near its upper end by line 16 and flows downwardly through the vessel contacting the feed to be treated. Fat solvent leaves from the lower end of the vessel by line 18 of the solvent circuit leading to a regeneration vessel 20 which the solvent enters at its upper end.

The regeneration vessel 20 shown here comprises a vertical column provided with a number of contacting trays 22 represented by broken lines.

The fat solvent will normally enter the column 3 to 5 trays from the top of the column and will flow downwardly through the trays in the regeneration zone 23 while being contacted by rising steam which is generated at the lower end of the column by means of a reboiler 24. The lean, regenerated absorbing solvent leaves from the bottom of the vessel by line 16 and is returned to the absorption vessel 10.

In general the absorption process takes place at between 40° and 60° C. and at super atmospheric pressure, whereas the regeneration step takes place at, e.g., at 140° C. at a pressure of 1½ to 2 bar. These conditions require the pressure of the fat solvent leaving the absorption vessel 10 by the line 18 to be reduced by a throttle 26 and, conversely, the lean solution to be repressurized before entering the absorption vessel 10.

In addition, a heat exchanger 30 enables the fat solvent to be partially heated by the returning hot, lean solvent. Further cooling of the lean solvent will generally be necessary and is carried out in a cooler 32.

The heat input of the reboiler 24 supplies the heat necessary for the slightly endothermic stripping reaction and the remainder, apart from losses, evaporates a part of the water present in the solvent. The resulting water vapor leaves by the top of the vessel 20 via line 34 with the acid gases released during the regeneration step to be recondensed in a cooler 36. The acid gases are separated from the resulting condensate in a separator 38 and leave for appropriate further treatment by line 40.

In general, the condensate is recombined with the lean solution in the solvent circuit at 42 downstream of the regenerator via liquid line 44. While the condensate can be returned to the lean solvent between the heat exchanger 30 and the cooler 32, the actual place where it is added back in the solvent circuit will largely depend upon its temperature. This will determine whether it is recombined upstream of the heat exchanger 30 or downstream of the cooler 32.

Some of the condensate may, however, be returned to the upper part of the regeneration vessel by line 46 so as to act as a water wash for the components leaving the regeneration vessel by the line 34. It may also be arranged to heat the cooler, incoming fat solvent entering by the line 18.

Where the solvet is highly concentrated it may alternatively be advantageous to return some or all of the condensate to the reboiler (by a dotted line 50) which will tend to stabilize the conditions in the latter and thus facilitate the control of the regeneration vessel. As a result, the relative partial pressure of the water vapor of the less highly concentrated solution in the reboiler is higher and prevents the temperature from fluctuating wildly as might otherwise occur.

Valve means (not shown) are provided for controlling the proportion of the condensate which is returned to the various points downstream (with respect to the solvent) of the regeneration zone.

FIG. 2 represents a unit similar to that of FIG. 1 but arranged so that a higher proportion (even all) of the condensate leaving the separator 38 can be recirculated to the upper part 54 of the vessel 20 by line 46. After descending about two tray levels, the condensate is trapped by a so-called total draw-off tray 52 which removes all the liquid at that level, thus preventing any of the condensate from entering the regeneration zone 23 of the vessel. This results in a much better washing of the gases leaving the regenerator and a reduced loss of solvent. The following calculated illustrations are given for a better understanding of the invention.

A concentrated absorbing solvent is circulated in a plant as described with reference to FIG. 1 of the drawing. The solvent comprises:

45 %w diisopropanolamine (DIPA)
40 %w sulfolane (cyclotetramethylene sulphone)
15 %w water.

Gas containing $H_2S$ as sole sour component is fed to the absorber and the $H_2S$ content of the treated gas is monitored.

The solvent is circulated at the rate of 100 parts w/h and 10 parts w/h saturated steam are supplied to the reboiler to maintain a regenerator bottom temperature of 140° C.

The regenerator is operated with and without reflux of the condensate in the regeneration zone, which amounts to 7 parts w/h. In the case where the condensate is not refluxed to the regeneration zone, it is cooled and recombined with the lean solvent downstream of the regenerator.

The solvent is fed to the absorber at 40° C. and the $H_2S$ content of the treated gas is 20 ppm in the case where the condensate is refluxed to the regenerator. The loading of the fat solvent is 0.35 mol $H_2S$/mol amine.

When the condensate is not reinjected into the regenerator but recombined with the lean solvent return stream, the $H_2S$ content of the treated gas gradually becomes leaner in $H_2S$. With no change in the steam flow to the regenerator a treated gas containing less than 15 ppm $H_2S$ may be obtained.

This indicates the improvement in the stripping in the regenerator when operated in accordance with the invention. It is important to note, however, that there should be sufficient trays both in the regenerator and in the absorber for the effect to be fully appreciated.

In the above illustration, the quantity of steam necessary to achieve a treated gas $H_2S$ content of 20 ppm is considered. As before, 10 parts w/h steam is required to achieve the specification in the conventional mode of operation where the condensate is refluxed to the upper part of the regenerator. However, it appears that where the condensate is removed and recombined with the lean solvent downstream of the regenerator, after equilibrium is reached, only 7.6 parts w/h steam are necessary to achieve the specification—a net saving of 24%.

In the event that some of the condensate is refluxed into the upper part of the regenerator as a water wash, this will increase the steam consumption unless it is withdrawn upstream of the regeneration zone. In general, where the reflux is not withdrawn above the regeneration zone, in order not to lose the benefit of the invention, the condensate refluxed to the reaction should be kept small—in the order of 1 part w/h in the case of the above illustration, which will provide sufficient wash water.

What is claimed is:
1. A process comprising
   (a) absorbing $H_2S$ from a gas stream containing said $H_2S$ by contacting the gas stream in an absorption zone with an absorbing solvent containing between 5 and 55 percent by weight of water, producing a treated gas and a fat solvent;
   (b) passing the fat solvent to a regenerator, and stripping the $H_2S$ from the fat solvent by contacting the fat solvent with steam, to produce a gas stream containing $H_2S$ and water vapor, and a lean absorbing solvent;
   (c) condensing the water vapor to form water and separating the water from the $H_2S$;
   (d) returning a portion of the water from step (c) to the upper section of the regeneration zone;
   (e) withdrawing water from said section, and combining the water with the lean absorbing solvent prior to entry of the lean absorbing solvent into the absorption zone;
   (f) and passing the lean absorbent and water to the absorption zone.
2. The process of claim 1 wherein the upper section of the regeneration zone is provided with a draw-off tray, and the water is removed by said tray.
3. The process of claim 1 in which the absorbing solvent comprises 10 percent to 35 percent water.
4. The process of claim 3 wherein the solvent comprises an alkanolamine or dialkanolamine solvent.

* * * * *